United States Patent [19]

Wilson et al.

[11] Patent Number: 5,705,379
[45] Date of Patent: Jan. 6, 1998

[54] NUCLEOTIDE SEQUENCES ENCODING A THERMOSTABLE ALKALINE PROTEASE

[75] Inventors: David B. Wilson, Ithaca, N.Y.; Guifang Lao, Bethesda, Md.

[73] Assignee: Cornell Research Foundation, Inc., Ithaca, N.Y.

[21] Appl. No.: 736,361

[22] Filed: Oct. 23, 1996

[51] Int. Cl.[6] .................. C12N 9/52; C12N 9/50; C12N 1/20; C07H 21/04
[52] U.S. Cl. ............... 435/220; 435/220; 435/252.3; 435/253.5; 435/320.1; 536/23.2
[58] Field of Search ............... 435/219, 220, 435/252.3, 253.5, 320.1; 536/23.2

[56] References Cited

U.S. PATENT DOCUMENTS 5,192,677  3/1993  Kinsella et al. .................. 435/220

OTHER PUBLICATIONS

Kristjansson and Kinsella, "Heat Stable proteinase from Thermomonospora fusca", Int. J. Peptide Protein Res. 36:201–207, 1990.

*Primary Examiner*—Robert A. Wax
*Assistant Examiner*—Elizabeth Slobadyansky
*Attorney, Agent, or Firm*—Hodgson, Russ, Andrews, Woods & Goodyear

[57] ABSTRACT

Nucleotide sequences, derived from a thermophilic actinomycete microorganism, which encode a thermostable alkaline protease are disclosed. Also disclosed are variants of the nucleotide sequences which encode a polypeptide having thermostable alkaline proteolytic activity. Recombinant thermostable alkaline protease or recombinant polypeptide may be obtained by culturing in a medium a host cell genetically engineered to contain and express a nucleotide sequence according to the present invention, and recovering the recombinant thermostable alkaline protease or recombinant polypeptide from the culture medium.

15 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1 :

( i ) SEQUENCE CHARACTERISTICS:
        ( A ) LENGTH: 1576 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:1 :

```
TCCGGAGCCA  CCCACATGGC  CAACGCCACC  GTACCGTGTC  GGAGAACTTG      50

CTGCTCGGTG  CAGGTGGAAT  TCCTCCGTGA  CGCACTGCAC  CTCACCTGAG     100

TGACCGCGGG  TTCTCGGCCT  CGGCGGGATC  GGACCGGTTT  TCGTCCGCCG     150

GGGCCGTGTT  TTTGGGACC   GCCCGGCATG  GTTTTGGCC   ACCCAGTGTA     200

CATAGAGTGT  CACCGGTTGT  CCGTTAGGTG  GTAGTGTCCC  TTTCGACTGA     250

CTGTCGAGAC  ACTCCACCGG  TGGGATGATG  GAGTCCCCCG  TCCGCCTGAC     300

TCCGACAACC  CAGGAAGGAA  CGGGTCGTGA  ACCATTCCTC  CCGAAGAACC     350

ACCTCCCTCC  TTTTCCACTG  CCGCCTGGCC  GCCACTGCAC  TGGTCGCCGC     400

CACCACCCCC  GCTCCGGCCC  AAGAGCTCGC  CCTCAAACGC  GACCTCGGGT     450

TGACGACGCT  GAAGTCGCGG  AACTGCGCGC  CGCCGAAGCC  GAAGCAGTCG     500

AGCTGGAAGA  GGACGTGCGC  GACTCCCTCG  GCTCCGATTT  CGGCCGTCTA     550

CTTGGACGCG  GACACCACAG  AGATCACGGT  CGCCGTCACC  GACCCCGCCG     600

CCGTGTCCCG  TGTCGACGCG  GACGACGTCA  CCGTGGACGT  TGTTGATTTC     650

GGGGAAACCG  CCCTCAACGA  CTTCGTGGCG  TCCCTCAACG  CGATCGCTGA     700

CACCGCTGAC  CCAAAGGTCA  CCGGCTGGTA  CACCGACCTG  GAGTCCCGAT     750

GCGGTAGTCA  TCACCACGCT  CCGGGGCGCA  CTCCGGCAGC  CGAAGAGCTC     800

GCCGAGCGGG  CTGGATCCTG  GACGACGCGG  GCCGTCGCGC  AATCTGTCGA     850

AGAGGACGAA  GAGCCGCAGT  CCCTTGCCGC  CATCATCGGC  GGCAACCCCT     900

ACTATTTCGG  GAACTACCGC  TGCTCTATCG  GATTCTCGGT  CCGCCAGGGC     950

AGCCAGACCG  GCTTCGCCAC  CGCGGGCCAC  TGCGGTTCGA  CAGGCACGCG    1000

AGTCAGCTCC  CCCTCAGGCA  CTGTCGCCGG  ATCGTACTTC  CCCGGCCGTG    1050

ACATGGGCTG  GGTGCGTATC  ACCAGCGCTG  ACACCGTCAC  CCCGCTCGTC    1100
```

| | | | | | |
|---|---|---|---|---|---|
| AACCGCTACA | ACGGCGGAAC | GGTGACCGTC | ACCGGTTCGC | AGGAGGCCGC | 1150 |
| CACCGGCTCT | TCGGTGTGCC | GCTCCGGGAG | CACCACCGGG | TGGCGCTGCG | 1200 |
| GCACCATCCA | GTCGAAGAAC | AGACCGTCC | GCTACGCGGA | AGGAACCGTC | 1250 |
| ACCGGCCTGA | CCCGCACCAC | TGCCTGCGCT | GAAGGCGACT | CCGGCGGCCC | 1300 |
| GTGGACCTGG | TTCCCAAGCC | CAAGGGTGAG | GGTGACCGGT | TCCAAGCCAA | 1350 |
| GGGTGACCTC | GGGGGGCAGC | GGTGACTGCG | GGTCCGGGGG | CATCACGTTC | 1400 |
| TTCCAGCCCA | TCAACCCGCT | GCTGTCCTAC | TTCGGACTGC | AACTGGTGGG | 1450 |
| ATGAGCCGGT | CTTCTCGGCC | CCGGGTTCCC | CTGTGTCCTC | GGGCCGCGGC | 1500 |
| GGTGGGCCCA | CCGATCTGAC | CAGTCACCCA | CCGTTAGGCT | GGAGCTATGC | 1550 |
| GTTCTGTTTC | GGCCGCCGTT | GTCGAC | | | 1576 |

( 2 ) INFORMATION FOR SEQ ID NO:2 :

( i ) SEQUENCE CHARACTERISTICS:
        ( A ) LENGTH: 17 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:2 :

AACCCCTATT ATTTTGG    17

( 2 ) INFORMATION FOR SEQ ID NO:3 :

( i ) SEQUENCE CHARACTERISTICS:
        ( A ) LENGTH: 965 nucleotides
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:3 :

| | | | | | |
|---|---|---|---|---|---|
| GTCGACGCGG | ACGACGTCAC | CGTGGACGTT | GTTGATTTCG | GGGAAACCGC | 50 |
| CCTCAACGAC | TTCGTGGCGT | CCCTCAACGC | GATCGCTGAC | ACCGCTGACC | 100 |
| CAAAGGTCAC | CGGCTGGTAC | ACCGACCTGG | AGTCCCGATG | CGGTAGTCAT | 150 |
| CACCACGCTC | CGGGGCGCAC | TCCGGCAGCC | GAAGAGCTCG | CCGAGCGGGC | 200 |
| TGGATCCTGG | ACGACGCGGG | CCGTCGCGCA | ATCTGTCGAA | GAGGACGAAG | 250 |
| AGCCGCAGTC | CCTTGCCGCC | ATCATCGGCG | GCAACCCCTA | CTATTTCGGG | 300 |
| AACTACCGCT | GCTCTATCGG | ATTCTCGGTC | CGCCAGGGCA | GCCAGACCGG | 350 |
| CTTCGCCACC | GCGGGCCACT | GCGGTTCGAC | AGGCACGCGA | GTCAGCTCCC | 400 |
| CCTCAGGCAC | TGTCGCCGGA | TCGTACTTCC | CCGGCCGTGA | CATGGGCTGG | 450 |
| GTGCGTATCA | CCAGCGCTGA | CACCGTCACC | CCGCTCGTCA | ACCGCTACAA | 500 |
| CGGCGGAACG | GTGACCGTCA | CCGGTTCGCA | GGAGGCCGCC | ACCGGCTCTT | 550 |
| CGGTGTGCCG | CTCCGGGAGC | ACCACCGGGT | GGCGCTGCGG | CACCATCCAG | 600 |
| TCGAAGAACC | AGACCGTCCG | CTACGCGGAA | GGAACCGTCA | CCGGCCTGAC | 650 |
| CCGCACCACT | GCCTGCGCTG | AAGGCGACTC | CGGCGGCCCG | TGGACCTGGT | 700 |

```
TCCCAAGCCC  AAGGGTGAGG  GTGACCGGTT  CCAAGCCAAG  GGTGACCTCG    750

GGGGGCAGCG  GTGACTGCGG  GTCCGGGGGC  ATCACGTTCT  TCCAGCCCAT    800

CAACCCGCTG  CTGTCCTACT  TCGGACTGCA  ACTGGTGGGA  TGAGCCGGTC    850

TTCTCGGCCC  CGGGTTCCCC  TGTGTCCTCG  GGCCGCGGCG  GTGGGCCCAC    900

CGATCTGACC  AGTCACCCAC  CGTTAGGCTG  GAGCTATGCG  TTCTGTTTCG    950

GCCGCCGTTG  TCGAC                                             965
```

( 2 ) INFORMATION FOR SEQ ID NO:4 :

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:4 :

```
ACGGTGACGT  CGTCCGCG    18
```

( 2 ) INFORMATION FOR SEQ ID NO:5 :

( i ) SEQUENCE CHARACTERISTICS:
        ( A ) LENGTH: 375
        ( B ) TYPE: amino acid
        ( C ) TOPOLOGY: linear ( i i ) MOLECULE TYPE: protein ( i i i ) SEQUENCE DESCRIPTION: SEQ ID NO:5 :

```
Val  Asn  His  Ser  Ser  Arg  Arg  Thr  Thr  Ser  Leu  Leu  Phe  His  Cys
 1                   5                        10                       15

Arg  Leu  Ala  Ala  Thr  Ala  Leu  Val  Ala  Ala  Thr  Thr  Pro  Ala  Pro
                    20                        25                       30

Ala  Gln  Glu  Leu  Ala  Leu  Lys  Arg  Asp  Leu  Gly  Leu  Thr  Thr  Leu
                    35                        40                       45

Lys  Ser  Arg  Asn  Cys  Ala  Pro  Pro  Lys  Pro  Lys  Gln  Ser  Ser  Trp
                    50                        55                       60

Lys  Arg  Thr  Cys  Ala  Thr  Pro  Ser  Ala  Pro  Ile  Ser  Ala  Val  Tyr
                    65                        70                       75

Leu  Asp  Ala  Asp  Thr  Thr  Glu  Ile  Thr  Val  Ala  Val  Thr  Asp  Pro
                    80                        85                       90

Ala  Ala  Val  Ser  Arg  Val  Asp  Ala  Asp  Asp  Val  Thr  Val  Asp  Val
                    95                        100                      105

Val  Asp  Phe  Gly  Glu  Thr  Ala  Leu  Asn  Asp  Phe  Val  Ala  Ser  Leu
                    110                       115                      120

Asn  Ala  Ile  Ala  Asp  Thr  Ala  Asp  Pro  Lys  Val  Thr  Gly  Trp  Tyr
                    125                       130                      135

Thr  Asp  Leu  Glu  Ser  Arg  Cys  Glu  Ser  His  His  His  Ala  Pro  Gly
                    140                       145                      150

Arg  Thr  Pro  Ala  Ala  Glu  Glu  Leu  Ala  Glu  Arg  Ala  Gly  Ser  Trp
                    155                       160                      165

Thr  Thr  Arg  Ala  Val  Ala  Gln  Ser  Val  Glu  Glu  Asp  Glu  Glu  Pro
                    170                       175                      180

Gln  Ser  Leu  Ala  Ala  Ile  Ile  Gly  Gly  Asn  Pro  Tyr  Tyr  Phe  Gly
                    185                       190                      195
```

| | | | | | | | | | | | | | |
|---|---|---|---|---|---|---|---|---|---|---|---|---|---|
|Asn|Tyr|Arg|Cys|Ser 200|Ile|Gly|Phe|Ser|Val 205|Arg|Gln|Gly|Ser|Gln 210|
|Thr|Gly|Phe|Ala|Thr 215|Ala|Gly|His|Cys|Gly 220|Ser|Thr|Gly|Thr|Arg 225|
|Val|Ser|Ser|Pro|Ser 230|Gly|Thr|Val|Ala|Gly 235|Ser|Tyr|Phe|Pro|Gly 240|
|Arg|Asp|Met|Gly|Trp 245|Val|Arg|Ile|Thr|Ser 250|Ala|Asp|Thr|Val|Thr 255|
|Pro|Leu|Val|Asn|Arg 260|Tyr|Asn|Gly|Gly|Thr 265|Val|Thr|Val|Thr|Gly 270|
|Ser|Gln|Glu|Ala|Ala 275|Thr|Gly|Ser|Ser|Val 280|Cys|Arg|Ser|Gly|Ser 285|
|Thr|Thr|Gly|Trp|Arg 290|Cys|Gly|Thr|Ile|Gln 295|Ser|Lys|Asn|Gln|Thr 300|
|Val|Arg|Tyr|Ala|Glu 305|Gly|Thr|Val|Thr|Gly 310|Leu|Thr|Arg|Thr|Thr 315|
|Ala|Cys|Ala|Glu|Gly 320|Asp|Ser|Gly|Gly|Pro 325|Trp|Thr|Trp|Phe|Pro 330|
|Ser|Pro|Arg|Val|Arg 335|Val|Thr|Gly|Ser|Lys 340|Pro|Arg|Val|Thr|Ser 345|
|Gly|Gly|Ser|Gly|Asp 350|Cys|Gly|Ser|Gly|Gly 355|Ile|Thr|Phe|Phe|Gln 360|
|Pro|Ile|Asn|Pro|Leu 365|Leu|Ser|Tyr|Phe|Gly 370|Leu|Gln|Leu|Val|Gly 375|

( 2 ) INFORMATION FOR SEQ ID NO:6 :

( i ) SEQUENCE CHARACTERISTICS:
 ( A ) LENGTH: 18 nucleotides
 ( B ) TYPE: nucleic acid
 ( C ) STRANDEDNESS: single- stranded
 ( D ) TOPOLOGY: linear ( i i ) MOLECULE TYPE: DNA ( i i i ) HYPOTHETICAL: No ( i v ) SEQUENCE DESCRIPTION: SEQ ID NO:6 :

ACCGGTGCGC AGGAGGCC       18

1

NUCLEOTIDE SEQUENCES ENCODING A THERMOSTABLE ALKALINE PROTEASE

This invention was made with government support under grant DE-F G02-13233 from the Department of Energy. The government has certain rights in the invention.

FIELD OF THE INVENTION

The present invention relates to nucleotide sequences comprising a gene or variants thereof which encode microbial alkaline proteases. More particularly, the invention is directed to a gene isolated from thermophilic actinomycete microorganisms, and variants of the gene, which encode a thermostable alkaline protease.

BACKGROUND OF THE INVENTION

Alkaline proteases have been isolated and/or characterized from a number of microbial sources including Bacillus species (see, e.g. U.S. Pat. Nos. 5,403,737; 5,399,283; 5,397,705; 5,387,518; 5,358,865; 5,352,604; 5,344,770; 5,275,945; and 5,217,878); Pyrococcus species (see, e.g. U.S. Pat. No. 5,391,489); Flavobacterium species (see, e.g., U.S. Pat. No. 4,429,044); and Actinomycete microorganisms (see, e.g., Nocardiopsis species as disclosed in U.S. Pat. No. 5,312,748; Thermomonospora species as disclosed in U.S. Pat. No. 5,192,677).

Alkaline proteases are used in industrial processes to catalyze the cleavage of peptide bonds. For example, such proteases are used as an additive to detergent solutions requiring enzyme activity in a pH range of from about 7 to about 10. Further, such proteases have been used in the food processing industry for the clarification of fruit juices, or for preparing hydrolyzed proteins as food additives or nutraceuticals. Other industrial applications for alkaline proteases include the production of pharmaceuticals, and for recovering silver from x-ray film by breaking down the film's gelatin layers. Alkaline proteases which exhibit thermostability, are desirable for those industrial processes which require proteolytic activity and that are optimally performed at high temperatures.

The amount of protease that can be made from a wild-type strain, as well as the rate of production of the protease, is generally insufficient for cost-effective commercial production. More efficient production of a protease, with a concomitant reduction in production cost, can often be achieved by producing the protease through recombinant means. In that regard, in some cases a microorganism other than the wild-type strain, can be genetically engineered such that an increased amount of protease is produced and/or the protease is produced in a manner which facilitates its isolation (as compared to production in the wild-type strain).

SUMMARY OF THE INVENTION

It is an object of the invention to provide a nucleotide sequence comprising a gene, isolated from an thermophilic actinomycete microorganism, which encodes a thermostable alkaline protease.

It is also object of the present invention to provide nucleotide sequences which are variants of the gene, and which encode a polypeptide having thermostable alkaline protease activity.

It is an object of the present invention to provide a means for recombinant producing a thermostable alkaline protease.

It is a further object of the present invention to provide expression vectors containing a nucleotide sequence that encodes a thermostable alkaline protease; or containing a nucleotide sequence which is a variant of the gene, and that encodes a polypeptide having thermostable alkaline protease activity.

It is an additional object of the present invention to provide recombinant host cells which contain multiple copies of a nucleotide sequence that encodes a thermostable alkaline protease, wherein the thermostable alkaline protease is recombinantly produced by culturing the recombinant host cells under suitable conditions.

Other objects, features, and advantages of the present invention will become apparent from the following drawings and detailed description.

DETAILED DESCRIPTION

Definitions

Figure 1:
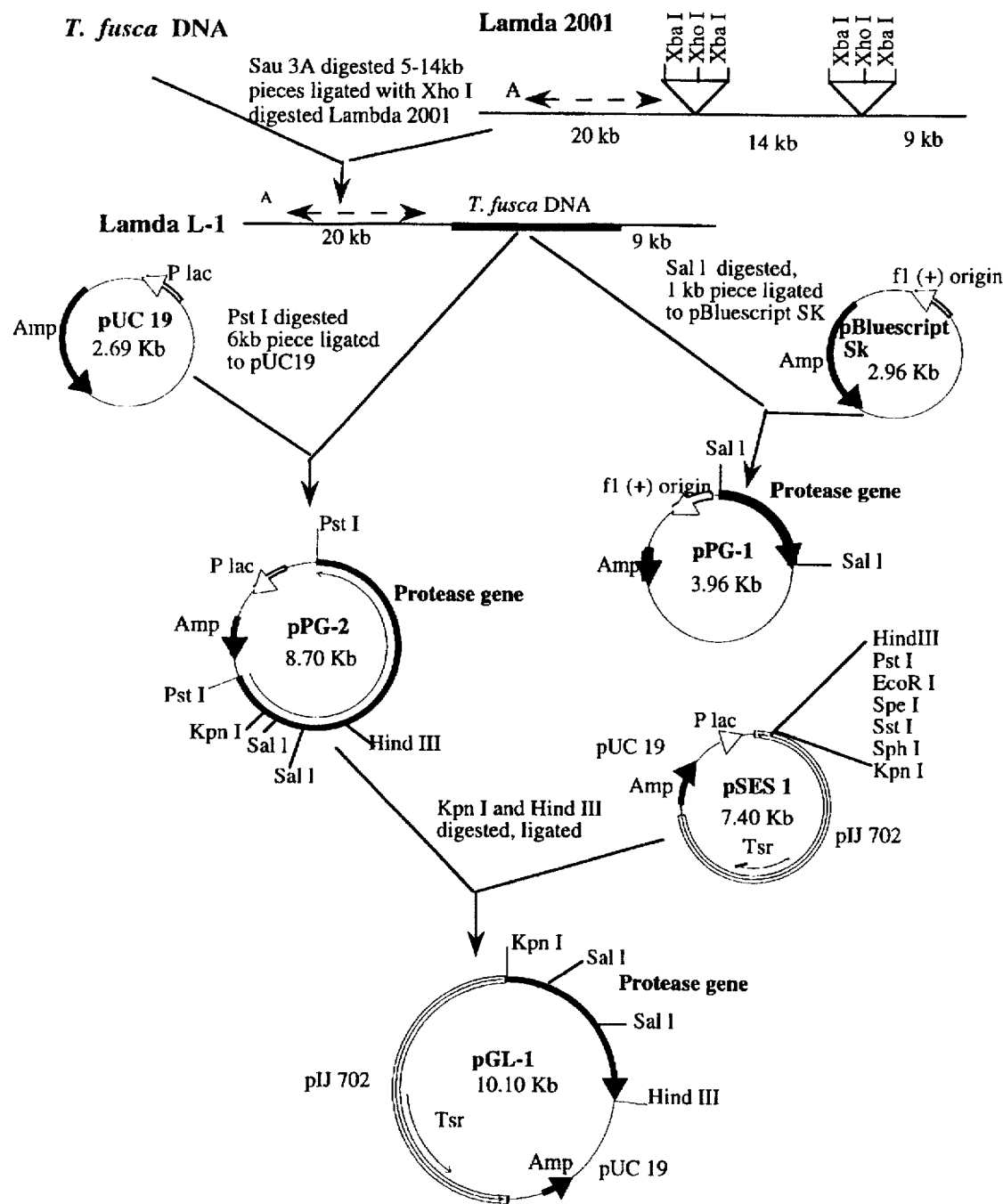
FIG. 1 is a flowchart depicting stages in the construction of various expression vectors for directing the expression of a gene, or variant sequence, encoding a thermostable alkaline protease.

"Prepro-peptide" or "prepro-region" are terms used hereinafter for the purposes of the specification and claims to refer to a sequence of amino acids bound to and located upstream from the N-terminal portion of the mature form of the thermostable alkaline protease, wherein the removal of this sequence results in the formation of the "mature form" of the thermostable alkaline protease. A prepro protein is a form of the thermostable alkaline protease containing the prepro-region. The prepro-region is made up of the pre-peptides (i.e., signal sequence) with the remainder of the region comprising the pro-peptide.

"Recombinant thermostable alkaline protease" is a term used hereinafter for the purposes of the specification and claims to refer to a thermostable alkaline protease produced from a microorganism other than from the family Actinomycete, wherein the microorganism has been genetically engineered to contain a nucleotide sequence isolated from an thermophilic cellulolytic actinomycete microorganism (or a variant of the nucleotide sequence) that encodes a thermostable alkaline protease. "Thermostable" or "thermostability" refers to the maintenance of substantial activity at temperatures above 60° C. for prolonged periods. "Alkaline" refers to retention of a majority of the enzyme's activity upon exposure to a pH in the range of from about 7 to about 12.

By the term "operably linked" is meant, for the purposes of the specification and claims to refer to the chemical fusion (restriction with subsequent ligation) or synthesis of heterologous DNA with a nucleotide sequence that encodes a thermostable alkaline protease such that the resultant recombinant DNA molecule is formed in a proper orientation and reading frame for the nucleotide sequence to be transcribed into functional RNA. In the construction of the recombinant DNA molecule, it is generally preferred to position a promoter at a distance upstream from the initial codon of the nucleotide sequence that is approximately the same as the distance in its natural setting (e.g., in the actinomycete microorganism). However, as known in the art, some variation in the distance can be accommodated without loss of promoter function. Likewise, it is generally preferred to position an enhancer element at a distance upstream from the promoter, or incorporated into the promoter sequences as a promoter element, or located between the promoter and the DNA molecule to be expressed. However, as known in the art, some variation in the placement can be accommodated without loss of the enhancer element's function.

By the term "expression vector" is meant, for the purposes of the specification and claims to refer to a DNA molecule which is operably linked to a nucleotide sequence that encodes a thermostable alkaline protease such that the production of the thermostable alkaline protease is effected in a suitable host. The vector may include, but is not limited to, a plasmid, phage, or a potential genomic insert.

By the terms "variant of the nucleotide sequence" or "variant of the gene" or "variant sequence" are meant, for the purposes of the specification and claims to refer to a nucleotide sequence that shares substantial homology (an identity of greater than about 85%) with SEQ ID NO. 1, or the open reading frame of SEQ ID NO:1 beginning at nucleotide 327 and ending at nucleotide 1451, encoding a thermostable alkaline protease. Such a sequence comparison can be performed using existing software known to those skilled in the art. Variants can be natural variants or variants produced by synthetic or mutagenic means for modifying the disclosed nucleotide sequences. With respect to such variations, and as appreciated by those skilled in the art, because of third base degeneracy, almost every amino acid can be represented by more than one triplet codon in a coding nucleotide sequence. Thus, a variant sequence be modified slightly in sequence (e.g., substitution of a nucleotide in a triplet codon), and yet still encode its respective gene product of the same amino acid sequence as encoded by the disclosed nucleotide sequences. Further, variant sequences may have minor base pair changes which may result in variation (conservative substitution) in the amino acid sequence encoded. Such conservative substitutions are not expected to substantially alter the biological activity of the gene product. A conservative substitution or modification of one or more amino acids are such that the tertiary configuration of the protease is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophantyrosine; aspartic acid-glutamic acid; arginine-lysine; asparagine-glutamine; and serine-threonine. Particularly relevant to amino acid substitutions in the α-helix which is located near or at the active site of the protease, a helix-forming amino acid may be replaced with another helix-forming amino acid. Helix-forming amino acids include alanine, leucine, methionine, glutamine, valine, and serine. A variant sequence may contain a modification, being defined functionally as resulting in a deletion of one or more amino acids which does not impart a change in the conformation, and hence the biological activity, of the thermostable alkaline protease that it encodes. Methods for synthetically producing such variant sequences are known to those skilled in the art of proteases (see, e.g. U.S. Pat. Nos. 5,403,737 and 5,275,945).

By the terms "consisting essentially of" or "comprising" a nucleotide sequence are meant, for the purposes of the specification and claims to refer to the base pair changes (substitution) in the nucleotide sequence such as a change in the third base of a triplet codon (third base degeneracy) or a change resulting in the encoding of a conservative substitution in the amino acid sequence encoded.

By the terms "consisting essentially of" or "comprising" an amino acid sequence are meant, for the purposes of the specification and claims to refer conservative substitutions in the amino acid sequence.

By the terms "% similarity" are meant, for the purposes of the specification and claims to refer to the percent of amino acids that are not identical, but similar (amino acids having substantially the same charge, size, hydrophilicity, and/or aromaticity) between two amino acid sequences as determined by sequence comparisons performed using algorithms known to those skilled in the art.

By the terms "% identity" are meant, for the purposes of the specification and claims to refer to the percent of amino acid positions that are identical between two amino acid sequences as determined by sequence comparisons performed using algorithms known to those skilled in the art.

The present invention relates to nucleotide sequences comprising a gene isolated from thermophilic actinomycete microorganisms, or variants of the gene, which encodes a thermostable alkaline protease. Generally, thermophilic actinomycetes are microorganisms that grow at temperatures between 32° C.–65° C. and are usually found growing in soil or vegetable substrates. Such thermophilic actinomycetes are recognized as a potentially enormous reservoir of thermostable enzymes such as enzymes having proteolytic, amolytic, lignolytic, peroxidase, neuramidase, cellulase, and xylanase activities (see, Sanglier et al., 1993, *Res. Microbiol.*, 144:661–3). Thermophilic actinomycetes include Thermoactinomyces, Streptomyces, Saccharopolyspora, Thermomonospora, and Microbispora species. Particularly relevant to this invention are species of thermophilic actinomyces that are cellulolytic microorganisms.

Most cellulolytic microorganisms produce one or more extracellular proteases that partially degrade their cellulases into multiple active isozymes. A common modification is the removal of a cellulose binding domain to produce a catalytic domain species. As a representative example of this phenomenon in thermophilic cellulolytic actinomycetes, *Thermomonospora fusca* (*T. fusca*) excretes an active thermostable protease that cleaves its cellulases into many isozymes, and the extracellular protease is synthesized at a higher level when the organism is utilizing cellulose as its carbon source. A native form (as opposed to a recombinant form) of such a thermostable protease has been described previously, by size and function, in U.S. Pat. No. 5,192,677 (assigned to the assignee of the present invention; the disclosure of which is hereby incorporated by reference). U.S. Pat. No. 5,192,677 discloses an exocellular thermostable alkaline protease isolated from *T. fusca* having optimal activity at about 80° C. and having a temperature range of from about 35° C. to about 95°, and optimal activity at about pH 9.0 and having a pH activity range from about 7 to 11.

In accordance with this invention, the nucleotide sequence of a gene encoding an active, extracellular thermostable alkaline protease isolated from a thermophilic cellulolytic actinomycetes is disclosed. The gene sequence described herein has been isolated from the thermophilic soil bacterium *T. fusca*. A nucleotide sequence of the present invention, SEQ ID NO:1, reveals that the encoded amino acid sequence contains a prepro-peptide of about 181 amino acid residues which is upstream of the about 194 amino acids encoding the mature protein of a calculated molecular weight of about 19 kilodaltons (kDa).

According to one embodiment of the present invention, using recombinant DNA techniques, a nucleic acid molecule containing the gene encoding the protease, or a variant of the gene encoding a catalytically active protease, is incorporated into an expression vector. The recombinant vector is then introduced into an appropriate host cell thereby directing the expression of the sequence in that particular host cell. The expression system, comprising the recombinant vector introduced into the host cell, can be used to produce recombinant thermostable alkaline protease, or a recombinant catalytically active polypeptide having thermostable alkaline protease activity, in the extracellular fluid from the culture. According to the present invention, recombinant thermostable alkaline protease, or a recombinant catalytically active polypeptide having thermostable alkaline protease activity, can be purified by methods known in the art including ion-exchange chromatography.

In another embodiment of the present invention one or more of the nucleic acid molecules of the invention, can be inserted into an expression vector that contains a nucleic acid molecule encoding another thermostable enzyme (e.g., cellulase), with the resultant expression vector being introduced into an appropriate host cell. Either the transformed host cell, the culture fluid therefrom, or a purified enzyme preparation can then be added directly to an industrial process for a sufficient time to decrease the amount of the target substrate(s) at a temperature which will enhance the enzymatic activity of the enzyme. A temperature range for such a process, and at which enzymatic activity is maintained, may be from approximately 35° C. to approximately 95° C. A pH range for such a process, and at which enzymatic activity is maintained, is a range of from pH 7–11. However, it will be apparent to those skilled in the art that the temperature and pH actually used necessarily depends on the particular process, and the inherent conditions at which the process must be, or desirably, is carried out. Further, the amount of time at which the substrate is exposed to, or treated with, the enzyme compositions of the present invention will vary depending on the amount of enzyme(s) used, the amount of substrate(s) contained in the process, the pH of the process, and the temperature at which the process is carried out.

For purposes of the description, the following embodiments illustrate the manner and process of making and using the invention and set forth the best mode contemplated by the inventor for carrying out the invention, but are not to be construed as limiting.

EXAMPLE 1

A gene encoding an extracellular, thermostable alkaline protease according to the present invention can be obtained by isolating the chromosomal DNA from a strain of thermophilic cellulolytic actinomycetes, constructing DNA probes having homology to putative DNA sequences encoding regions of the gene, preparing genomic libraries from the isolated chromosomal DNA, and screening the libraries for the gene of interest by hybridization to the probes. The genomic libraries can be constructed using vectors (e.g., bacteriophage), host cells (e.g. *Escherichia coli*), and methods known to those skilled in the art. Such oligonucleotide probes having DNA sequence identity with a portion of SEQ ID NO:1 can be used to probe for a gene encoding an extracellular, thermostable alkaline protease according to the present invention.

In one illustration of this embodiment, a gene encoding an extracellular, thermostable alkaline protease according to the present invention was isolated, and identified, from *T. fusca*. The strategy used to clone the gene encoding an extracellular, thermostable alkaline protease was to purify the mature protease from *T. fusca* strain YX culture supernatant, determine a portion of the N-terminal sequence of the protease, and synthesize a degenerate probe which could be used to identify the gene encoding the protease in restricted *T. fusca* DNA by hybridization analysis. A degenerate probe (as illustrated by one representative sequence, SEQ ID NO:2) was synthesized accordingly. The degenerate probe, designed to have sequence identity for a nucleotide sequence encoding the 8th to the 13th amino acid residues of the N-terminus of the mature *T. fusca* protease, was end labeled with digoxigenin-dUTP using terminal transferase.

A genomic library was constructed by partial digestion of *T. fusca* chromosomal DNA with restriction enzyme Sau3A and then reacted with Klenow polymerase in the presence of ATP and GTP. Fragments of the desired size were isolated by gradient centrifugation, and then ligated to lambda phage arms which had been digested with XhoI and reacted with Klenow polymerase in the presence of CTP and TTP. The ligation mixture was then packaged. The resultant recombinant phage were used to infect *E. coli* DH5α, which then were plated on tryptone broth agar plates. The labeled oligonucleotide probe was used to screen filters containing DNA of the plaques formed. The probe was hybridized to the filters at 42° C. for 10 hours, followed by washing the filters with 6×SSC and 0.01% (once at room temperature, and twice at 42° C. for 15 minutes). Plaques that hybridized to the labeled probe (15 "positive clones" from screening approximately 15,000 plaques) were further purified. Recombinant phage DNA from the respective positive clones was purified using a commercially available kit.

All of the positive clones contained a 2.7 kilobase (kb) XhoI-XhoI fragment that hybridized to this probe. A band of approximately 1 kb, that hybridized to the probe, was generated using SalI. The 1.0 kb fragment was isolated and ligated into a plasmid (pBluescript SK+). Competent *E. coli* strain JM109 was transformed with the recombinant plasmid (termed pPG-1; See FIG. 1). The sequence of the insert of pPG-1 was determined using the standard dideoxy chain termination method. Further, formamide (20%, vol/vol) was added to the 6% polyacrylamide gels to resolve the secondary structure due to a high G+C content. The resulting sequence, shown as SEQ ID NO:3, showed that the 5' end of the gene was missing.

A second oligonucleotide probe, an 18 mer shown as SEQ ID NO:4 was prepared based on the DNA sequence from the 5' end of the 1.0 kb SalI fragment (SEQ ID NO:3). This second probe was also end labeled with digoxigenin-dUTP using terminal transferase. The second probe was used to screen the genomic library for plaques by hybridization. A 6.0 kb Pst I fragment was isolated and ligated into a plasmid (pUC19) in forming pPG2, as illustrated in FIG. 1. Sequencing of the insert of pPG-2 identified the rest of the open reading frame of the gene encoding the thermostable alkaline protease. Taken together, the sequence data showed that this entire protease gene was present in an approximately 1.8 kb KpnI-HindIII fragment.

EXAMPLE 2

A nucleotide sequence comprising a gene encoding an extracellular, thermostable alkaline protease according to the present invention, obtained by from screening a genomic library made from a strain of thermophilic cellulolytic actinomycetes, can be further characterized by computer analysis using software known in the art to record the DNA sequence and determine the correct reading frame, codon usage, and predicted amino acid sequence and molecular size of the encoded protein. The nucleotide sequence of the coding region (open reading frame) of the gene encoding the thermostable alkaline protease is 1127 nucleotides that starts with a GTG initiation codon (nucleotide position 327 of SEQ ID NO:1) and terminates with a TAG stop codon (at nucleotide position 1454 of SEQ ID NO:1) which is flanked by a 14-bp inverted repeat sequence. This coding sequence is characteristic of a *T. fusca* gene—a high overall G+C content of about 65% and a strong tendency to utilize codons that have G or C in the third position of a triplet codon. Primer extension determined that the transcriptional start codon is located 19 nucleotides upstream of the translational initiation codon. The size of the mRNA was determined by Northern gel analysis to be about 1.1 kb.

The gene encodes a polypeptide chain of 375 amino acid residues (SEQ ID NO:5), with a prepro region comprising the first 181 amino acid residues. The molecular weight of the mature protein (amino acid residues 182 to 375), as calculated from SEQ ID NO:5, is 19 kDa which is close to the value determined by sodium dodecyl polyacrylamide gel electrophoresis (SDS-PAGE) of 18.7 kDa. A prepro-region has been commonly observed in the N-terminal region of genes encoding bacterial serine proteases, and typically range in size of from about 114 to about 198 residues in the encoded protein. The signal sequence (amino acids 1–31 of SEQ ID NO:5) of the protease contains 31 amino acids, including a hydrophobic region and a potential signal peptide cleavage site comprising two alanine residues separated by another amino acid which are typical of actinomycete signal sequences. A sequence comparison was made between the prepro-region from members of the serine protease family: from a thermostable alkaline protease encoded by a gene according to the present invention, from the α-lytic protease from *Lysobacter enzymogenes*, from the glutamic acid-specific protease of *Streptomyces fradiae*, and from the proteases A and B from *S. griseus*. The range of identity between the amino acid sequence of the prepro region of a thermostable alkaline protease encoded by a gene according to the present invention and these other serine proteases ranged from 18–45%. It was clear from this comparison that many similar residues in the prepro-region are conserved amongst these proteases, which may reflect a common mechanism for folding the respective protease into its active conformation.

A sequence comparison was made between the mature enzymes from members of the above-identified serine proteases. The range of identities of the five mature proteases compared is from 39% to 47%, as shown in Table 1. Histidine, aspartic acid, and serine are catalytic residues found in most serine proteases. These catalytically-involved triad residues were found to be conserved in all five protease sequences compared. In the exemplary thermostable alkaline protease encoded by a gene according to the present invention, the catalytically-involved triad are found at residues 218 (His), 242 (Asp), and 322 (Ser) of SEQ ID NO:5. Additionally, the exemplary thermostable alkaline protease encoded by a gene according to the present invention has six cysteine residues in the mature enzyme (residues 199, 219, 281, 291, 317, and 351 of SEQ ID NO:5), in positions identical with those of α-lytic protease, which form three disulfide bonds that play a role in three dimensional structure.

TABLE 1

| Proteases compared | Length (aa) | % identity | % similar | Gap* | aa region |
|---|---|---|---|---|---|
| Mature enzyme: | | | | | |
| *T. fusca*** | 194 | 39 | 54 | 3 | 5-193 |
| *S. griseus*[a] | 190 | | | | 1-181 |
| *T. fusca* | | 47 | 61 | 6 | 5-192 |
| *S. griseus*[b] | 196 | | | | 1-184 |
| *T. fusca* | | 41 | 56 | 4 | 5-192 |
| *S. fradiae*[c] | 195 | | | | 1-186 |
| *T. fusca* | | 47 | 60 | 5 | 2-194 |
| *L. enzymogenes*[d] | 198 | | | | 1-197 |
| Pro-peptides: | | | | | |
| *T. fusca* | 150 | 18 | 43 | 3 | 3-149 |
| *L. enzymogenes* | 155 | | | | 25-166 |
| *T. fusca* | | 24 | 42 | 4 | 24-107 |
| *S. griseus*[a] | 84 | | | | 1-78 |
| *T. fusca* | | 26 | 43 | 3 | 30-107 |
| *S. griseus*[b] | 79 | | | | 4-76 |
| *T. fusca* | | 29 | 49 | 3 | 7-149 |
| *S. fradiae* | 143 | | | | 1-129 |
| Pre-peptides: | | | | | |
| *T. fusca* | 31 | 45 | 55 | 0 | 2-21 |
| *L. enzymogenes* | 20 | | | | 5-24 |
| *T. fusca* | | 38 | 54 | 1 | 6-31 |
| *S. griseus*[a] | 31 | | | | 4-34 |
| *T. fusca* | | 28 | 41 | 0 | 2-30 |
| *S. griseus*[b] | 29 | | | | 10-38 |
| *T. fusca* | | 29 | 42 | 0 | 1-31 |
| *S. fradiae* | 31 | | | | 1-31 |

Length width = 0.1
*Gap weight = 3
**thermostable alkaline protease
[a]*S. griseus* protease A
[b]*S. griseus* protease B
[c]*S. fradiae* protease
[d]*L. enzymogenes* α-lytic protease

EXAMPLE 3

The present invention relates to a gene, isolated from a strain of thermophilic cellulolytic actinomycetes, wherein such a gene encodes an extracellular, thermostable alkaline protease. With sequence information, like that shown in SEQ ID NOs: 1, 3 and 5, other polypeptides can be produced which display thermostable alkaline protease activity. Variant nucleotide sequences can be natural variants or variants produced by synthetic or mutagenic means for modifying the disclosed nucleotide sequences. Methods for synthetically producing such variant sequences are known to those skilled in the art of proteases. In designing such variants, one needs to consider avoiding mutations of sequences that encode the catalytically-involved amino acids or the cysteine residues involved in disulfide bond formation, and which would negatively affect the resultant thermostable alkaline protease activity. In that regard, it is noted that the substrate-binding pocket (also called the "hydrophobic pocket") appears to include the mildly non-polar side chains Gly, Gly, and Cys (positions 270, 319, 291, respectively, of SEQ ID NO:5), which make it a suitable environment for the binding of the non-polar or hydrophobic side chains of the substrate.

In one embodiment, the variant sequence may be produced by site-directed mutagenesis using one of the several methods for such mutagenesis which are known to those skilled in the art (see, e.g. U.S. Pat. No. 5,397,705) For example, site directed mutagenesis using oligonucleotides comprises the steps of (i) synthesizing an oligonucleotide with a sequence nearly identical to a sequence found in SEQ ID NO:1 except that the oligonucleotide sequence contains the desired nucleotide substitution (encoding for a mutation in the amino acid sequence); (ii) hybridizing the oligonucleotide primer to a template comprising the nucleotide sequence encoding a thermostable alkaline protease; and extending the oligonucleotide primer using a DNA polymerase. The resultant variant sequence may then be incorporated into an expression vector which is then used to genetically engineer a host cell to recombinantly produce a polypeptide having thermostable alkaline protease activity. As an example, a variant may be constructed to produce a polypeptide which displays thermostable alkaline protease activity, wherein the polypeptide contains a substitution for serine at position 271 of SEQ ID NO:5. In this example, mutagenesis of Ser 271 to Ala may be directed by a 18 mer oligonucleotide primer having the sequence of SEQ ID NO:6. The primer includes a sequence from SEQ ID NO:1 that encodes amino acids 269 through 274 of SEQ ID NO:5 except that the TCG codon encoding serine was substituted with the GCG codon encoding alanine.

In another embodiment, genetic engineering techniques can be used to generate nucleic acid molecules comprising a variant sequence that is a substantial portion of SEQ ID NO:1. As apparent to one skilled in the art, from the sequence disclosed as SEQ ID NO:1 and from the restriction maps illustrated in FIG. 1, it can be determined which restriction enzyme or combination of restriction enzymes may be used to generate nucleic acid molecules encoding catalytically active polypeptide having thermostable alkaline protease activity. Restriction enzyme selection may be done so as not to destroy the catalytically active domain and the hydrophobic pocket of the resultant polypeptide. Consequently, using SEQ ID NO:1 as a guide, restriction enzyme combinations may be used to generate nucleic acid molecules (variant sequences), which when inserted into the appropriate vector, are capable of directing the production of catalytically active polypeptide having thermostable alkaline protease activity.

EXAMPLE 4

This embodiment illustrates that a nucleic acid molecule comprising a nucleotide sequence encoding a thermostable alkaline protease, or a variant sequence encoding a polypeptide having thermostable alkaline protease activity, can be inserted into various vectors including phage vectors and plasmids. Successful expression of the thermostable alkaline protease, or a polypeptide having thermostable alkaline protease activity (each hereinafter referred to as "recombinant protease"), requires that either the insert comprising the gene encoding the thermostable alkaline protease, or a variant sequence encoding a polypeptide having thermostable alkaline protease activity, or the vector itself, contain the necessary elements for transcription and translation (expression control elements) which is compatible with, and recognized by the particular host system used for expression. A variety of host systems may be utilized to express the recombinant protease, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the nucleic acid molecule encoding the recombinant protease, to increase the expression of the recombinant protease, provided that this increased expression is compatible with (for example, non-toxic to) the particular host cell system used. Thus and importantly, the nucleic acid molecule can consist of the gene or the variant sequence encoding the recombinant protease. The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene or the variant sequence and expression into the recombinant protease product. For example, bacterial, phage, or plasmid promoters known in the art from which a high level of transcription has been observed in a host cell system comprising $E.\ coli$ include the lac promoter, trp promoter, tac promoter, recA promoter, ribosomal RNA promoter, the $P_R$ and $P_L$ promoters, lacUV5, ompF, bla, lpp, and the like, may be used to provide transcription of the inserted DNA sequence encoding the recombinant protease.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted nucleic acid molecule encoding the recombinant protease to increase transcriptional efficiency. As illustrated in Example 2 and as apparent from SEQ ID NO:1, other specific regulatory sequences have been identified which may effect the expression from the gene or the variant sequence encoding the recombinant protease. These or other regulatory sites, such as transcription or translation initiation signals, can be used to regulate the expression of the gene or the variant sequence encoding the recombinant protease. Such regulatory elements may be inserted into nucleic acid molecules encoding the recombinant protease or nearby vector DNA sequences using recombinant DNA methods described for insertion of DNA sequences.

Accordingly, nucleic acid molecules containing regions encoding for the recombinant protease can be ligated into an expression vector at a specific site in relation to the vector's promoter, control, and regulatory elements so that when the recombinant vector is introduced into the host cell, the recombinant protease is expressed from the recombinant vector in the host cell. For example, the gene or the variant sequence containing its own regulatory elements can be ligated into an expression vector to operably link the gene or variant sequence to the vector promoter, and control elements which will allow for expression of the recombinant protease. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid; immunoscreening for production of recombinant protease-specific epitopes using antisera generated to specific epitopes of the protease; probing the DNA of the host cells for protease-specific nucleic acid molecules using one or more oligonucleotides and methods described according to Example 1 herein; and a protease activity assay.

Figure 2:
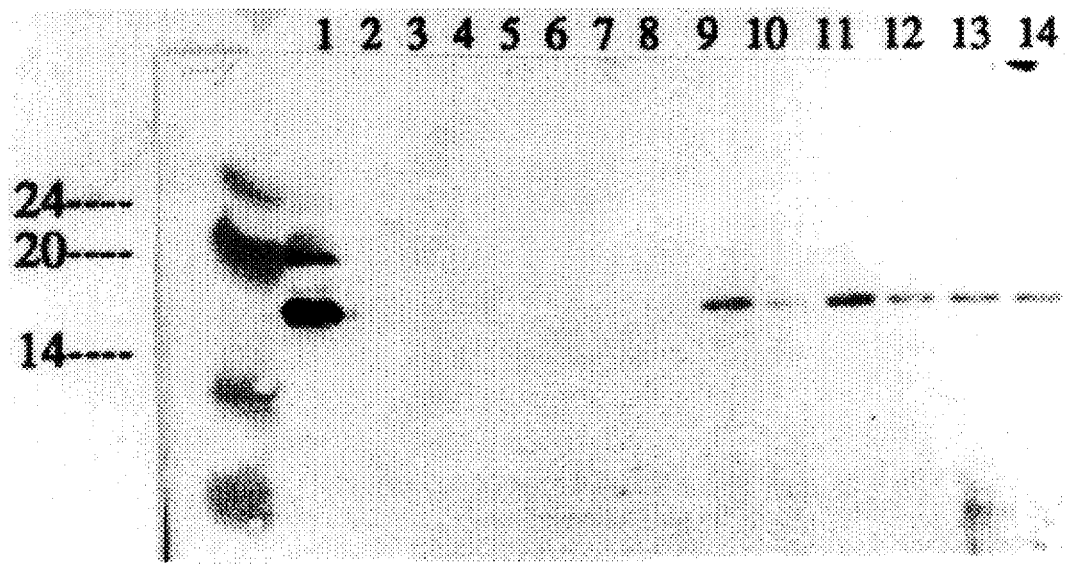
FIG. 2 is a photograph of a Western blot showing *T. fusca* thermostable alkaline protease purified from *T. fusca* (lane 1); supernatant from *S. lividans* (lanes 3 & 4); extracts of *E. coli* transformed with pGL-1 (lanes 5 & 6); extracts of *E. coli* transformed with pPG-1 (lane 7); extracts of *E. coli* transformed with pPG-2 (lane 8); supernatants from *S. lividans* transformed with pGL-1 (lanes 9–14).

Plasmids constructed to express recombinant protease are illustrated in FIG. 1. As shown in SEQ ID NO:3 for the insert of pPG-1, the 5' end of the gene encoding a thermostable alkaline protease was missing. However, the 6.0 kb insert of pPG-2 contains the entire protease gene. Competent $E.$ $coli$ were transformed with either pPG-1 or pPG-2, and selected for amp resistance. Bacterial extracts from log phase cultures were analyzed for recombinant protease expression by SDS-PAGE and Western blot using a polyclonal antiserum having binding specificity for the thermostable alkaline protease. As shown in FIG. 2, Western blotting of $E.$ $coli$ transformed with either pPG1 (lane 7) or pPG2 (lane 8) using antiserum to $T.$ $fusca$ protease did not detect production of recombinant protease. The observed lack of detectable expression may be due to either the lack of correct folding of the recombinant protease, or to the selection or placement of a promoter which may not be optimum for expression.

For expression of recombinant protease in $Streptomyces$ $lividans$, an $E.$ $coli$-$S.$ $lividaris$ shuttle plasmid, pGL-1, was constructed as illustrated in FIG. 1. pGL-1 contains a 2.7 kb insert, derived from pPG-2, which contains the entire gene encoding a thermostable alkaline protease. To express the recombinant protease in $S.$ $lividans$, pGL-1 was transformed into $S.$ $lividans$ strain TKM31 (a protease-negative strain isolated from $S.$ $lividans$ TK24) protoplasts, selecting for thiostrepton (50 µg/ml) resistance (tsr). Transformants were grown on phosphate starvation agar plates containing 1% casein and 1% gelatin, and transformants containing protease activity formed distinct white rings around the colonies after 3 to 5 days of growth at 37° C. Active transformants were checked for stability by repeated passage, selection, and screening.

Supernatants from log phase cultures of the $S.$ $lividans$ transformants were analyzed for recombinant protease expression by SDS-PAGE and Western blot using a polyclonal antiserum having binding specificity for the thermostable alkaline protease. As shown in FIG. 2, western blotting of $S.$ $lividans$ containing pGL-1 (lanes 9-14) confirmed that the protease gene was expressed in $S.$ $lividans$, and the recombinant protease was secreted. A second plasmid, pGL-2 was constructed from pGL-1 by changing, in relation to the orientation tsr promoter, the alignment of the KpnI-HindIII fragment. $S.$ $lividans$ containing pGL-2 also expressed the protease gene, and the recombinant protease was secreted. Thus, the orientation of the tsr promoter had no effect on the expression of the protease gene in $S.$ $lividans$, suggesting that the promoter of the protease gene was active in $S.$ $lividans$.

Figure 3:
FIG. 3 is a photograph of a Western blot showing supernatant from wild-type *S. lividans* protease transformants (lanes 1–3); supernatant from protease inhibitor deficient mutants of *S. lividans* protease transformants (lanes 4 & 5); recombinant protease purified from *S. lividans* transformed with pGL-1 (lane 6); native *T. fusca* thermostable alkaline protease (lane 7).

The recombinant protease may also be expressed in a protease inhibitor-deficient host cell. For example, many extracellular proteins that inhibit proteases have been found to be produced by actinomycetes. Protease inhibitor-deficient mutants can be isolated by screening the host cells for the lack of protease inhibitor activity (see, e.g., Taguchi et al., 1993, $Appl.$ $Environ.$ $Microbiol.$ 59:4338–4341). Expression of the recombinant protease was examined in a $S.$ $lividans$ protease inhibitor-deficient mutant, and compared to expression from a wild-type transformant. As shown in FIG. 3, recombinant protease expressed by wild type transformants (lanes 2 and 3) migrated differently than recombinant protease produced from the protease inhibitor-deficient mutant (lanes 4 & 5). These results indicate that there is an interaction between this recombinant protease encoded by a $T.$ $fusca$ gene, and a protease inhibitor in $S.$ $lividans$ that is not present in a protease inhibitor-deficient mutant. Further experiments showed that this protease inhibitor could be inactivated at temperatures above 45° C. Thus, depending on the desired host cell expression system, it may be advantageous to express the recombinant protease in either a protease inhibitor-deficient host cell, or under conditions in which the protease inhibitor is inactivated.

EXAMPLE 5

This embodiment illustrates that a recombinant thermostable alkaline protease encoded by a nucleic acid molecule according to the present invention, or a recombinant polypeptide having thermostable alkaline protease activity encoded by a variant sequence according to the present invention, can be purified from the host cell expression system. In this illustration, the recombinant protease was purified from a culture of $S.$ $lividans$ transformed with pGL-1. In order to keep the recombinant protease in solution during purification, 1 mM $MgCl_2$ was always present. Similarly, during concentration of the recombinant protease, 0.2M $MgCl_2$ was present. All purification procedures were conducted at 4° C. to prevent autolysis of the recombinant protease. A 25 ml culture of transformed $S.$ $lividans$ was grown in the presence of tsr (5 µg/ml) for 3 days at 30° C. The culture was then used to inoculate a 250 ml culture, and grown at 30° C. for 24 hours. The entire culture was added to 10 liters of medium and grown in a fermentor (agitation: 200 rpm; temperature: 30° C.; initial pH 7.1; air flow: 1 volume of air per volume of medium per minute). The highest proteolytic activity in the supernatant occurred at about 60 hours.

The 60 hour supernatant was filtered by cross-flow filtration with 0.45 micron membranes. The clear protease-containing supernatant was salted out with 80% $(NH_4)_2SO_4$ and centrifuged at 10,000×g for 20 minutes. The redissolved recombinant protease pellet was dialyzed against HM buffer (0.01M Hepes, 1 mM $MgCl_2$, pH 7.3) for 3 hours with three changes (one change per hour). After dialysis, the sample was adjusted to pH 5.9 and diluted with water to a conductivity of 1.2 micro-mho. The 400 ml sample was loaded on a cation exchange column which was equilibrated with HM buffer, pH 5.9. The column was then washed with HM buffer, pH 5.9 until the OD 280 was constant. The recombinant protease was eluted with a linear gradient of NaCl (0 to 0.25M) in HM buffer, pH 7.5, and the proteolytic activity of each fraction was assayed.

Proteolytic activity was assayed using 1% sulfanilamide-azocasein dissolved in 0.1M Tris/HCl buffer pH 8.0 at 65° C. for 30 minutes, and the reaction was stopped by the addition of one third volume of 5% trichloroacetic acid. The clarified supernatant containing the nonprecipitable azopeptides produced by protease activity was analyzed spectrophotometrically at 440 nm. One unit of protease activity is defined as a change in OD of 0.1 per minute at 65° C. The specific activity of the purified recombinant protease was 55 units/mg. On SDS gel electrophoresis, the purified recombinant protease preparation appeared as a single band. The purified recombinant exhibited broad specificity, temperature stability (35° C. to 95° C., with optimal activity at 80° C.); pH range (about 7 to about 11, with an optimum pH value of 9.0), and SDS resistance.

EXAMPLE 6

This embodiment illustrates that a purified recombinant thermostable alkaline protease, encoded by a nucleic acid molecule according to the present invention, or a purified recombinant polypeptide having thermostable alkaline protease activity, encoded by a variant sequence according to the present invention, can be used in various applications to catalyze the cleavage of peptide bonds. For example, such a recombinant thermostable alkaline protease may be used as an additive to detergent solutions requiring enzyme activity in a pH range of from about 7 to about 10 to remove protein-based stains (See, e.g. *The Economist*, Mar. 4, 1989, p.80; U.S. Pat. Nos. 5,275,945 and 5,358,865). Further, such proteases have been used in a method for cleaning contact lenses (See, e.g. U.S. Pat. No. 5,409,546), to clean filtration membranes used to concentrate milk (*The Economist*, supra), to break down the gelatin layers of used X-ray film in a process to recover silver (*Business Week*, Jan. 22, 1996, p.94), as well as various industrial applications.

Having described the preferred embodiments of the present invention, it will be apparent to one of ordinary skill in the art that various modifications may be made to the disclosed embodiments, and that such modifications are intended to be within the scope of the present invention.

What is claimed is:

1. An isolated nucleic acid molecule comprising a nucleotide sequence, wherein the nucleotide sequence is selected from the group consisting of:
   (a) SEQ ID NO:1 encoding a thermostable alkaline protease,
   (b) a portion of SEQ ID NO:1 which is at least 17 bp and specifically hybridizes to SEQ ID NO:1, and
   (c) a variant sequence of SEQ ID NO:1 encoding a polypeptide having thermostable alkaline protease activity, wherein said variant sequence has a sequence identity of greater than about 85% with SEQ ID NO:1 or with the open reading frame of SEQ ID NO:1 beginning at nucleotide 327 and ending at nucleotide 1451 of SEQ ID NO:1.

2. The nucleic acid molecule of claim 1, wherein the nucleotide sequence consists of a gene having an open reading frame beginning at nucleotide 327 of SEQ ID NO:1 and ending at nucleotide 1451 of SEQ ID NO:1.

3. The nucleic acid molecule according to claim 1, wherein the nucleotide sequence encodes a protein selected from the group consisting of a preproprotein and a mature protein, wherein the preproprotein consists of an amino acid sequence shown in SEQ ID NO:5, and wherein the mature protein consists of an amino acid sequence of from amino acid residue 182 to amino acid residue 375 of SEQ ID NO:5.

4. A recombinant expression vector containing the nucleic acid molecule of claim 1.

5. A recombinant expression vector containing the nucleic acid molecule of claim 2.

6. A genetically engineered host cell containing the recombinant vector according to claim 4.

7. A genetically engineered host cell containing the recombinant vector according to claim 5.

8. A method for producing a protein selected from the group consisting of a thermostable alkaline protease and a polypeptide having thermostable alkaline protease activity in a host cell, said method comprising:
   (a) growing a genetically engineered host cell according to claim 6 in culture medium for a sufficient time, and under suitable conditions, to produce a recoverable quantity of the protein; and (b) recovering the protein from the culture medium.

9. The method according to claim 8, wherein the host cell is a protease inhibitor deficient host cell.

10. The method according to claim 8, wherein the host cell is a strain of Streptomyces.

11. The method according to claim 8, wherein in the recovery of the protein from the culture medium, a sufficient amount of $MgCl_2$ is present to keep the protein in solution.

12. A method for producing a protein selected from the group consisting of a thermostable alkaline protease and a polypeptide having thermostable alkaline protease activity in a host cell, said method comprising:

(a) growing a genetically engineered host cell according to claim 7 in culture medium for a sufficient time, and under suitable conditions, to produce a recoverable quantity of the protein; and (b) recovering the protein from the culture medium.

13. The method according to claim 12, wherein the host cell is a protease inhibitor-deficient host cell.

14. The method according to claim 12, wherein the host cell is a strain of Streptomyces.

15. The method according to claim 12, wherein in the recovery of the protein from the culture medium, a sufficient amount of $MgCl_2$ is present to keep the protein in solution.

* * * * *